United States Patent
Giuliani et al.

(10) Patent No.: US 9,144,560 B2
(45) Date of Patent: Sep. 29, 2015

(54) COMPOSITION COMPRISING RUTIN AND POLYUNSATURATED FATTY ACID HAVING AN INHIBITORY ACTIVITY ON 5 α-REDUCTASE

(75) Inventors: Giammaria Giuliani, Milan (IT); Anna Benedusi, Milan (IT); Sergio Baroni, Milan (IT)

(73) Assignee: GIULIANI S.P.A., Milan (IT)

( * ) Notice: Subject to any disclaimer, the term of this patent is extended or adjusted under 35 U.S.C. 154(b) by 1170 days.

(21) Appl. No.: 12/450,362

(22) PCT Filed: Mar. 18, 2008

(86) PCT No.: PCT/IB2008/000772
§ 371 (c)(1),
(2), (4) Date: Oct. 7, 2009

(87) PCT Pub. No.: WO2008/114141
PCT Pub. Date: Sep. 25, 2008

(65) Prior Publication Data
US 2010/0034904 A1    Feb. 11, 2010

(30) Foreign Application Priority Data
Mar. 21, 2007  (IT) .............................. MI2007A0555

(51) Int. Cl.
| | | |
|---|---|---|
| *A61K 36/00* | (2006.01) | |
| *A61K 36/30* | (2006.01) | |
| *A61K 31/201* | (2006.01) | |
| *A61K 8/37* | (2006.01) | |
| *A61K 8/60* | (2006.01) | |
| *A61K 8/92* | (2006.01) | |
| *A61K 31/202* | (2006.01) | |
| *A61K 31/7048* | (2006.01) | |
| *A61Q 5/00* | (2006.01) | |

(52) U.S. Cl.
CPC ................. *A61K 31/201* (2013.01); *A61K 8/37* (2013.01); *A61K 8/602* (2013.01); *A61K 8/922* (2013.01); *A61K 31/202* (2013.01); *A61K 31/7048* (2013.01); *A61Q 5/00* (2013.01)

(58) Field of Classification Search
CPC ............................... A61K 36/00; A61K 36/30
USPC .................................... 424/776, 778
See application file for complete search history.

(56) References Cited

U.S. PATENT DOCUMENTS

| | | | | |
|---|---|---|---|---|
| 4,888,326 | A | * | 12/1989 | Horrobin ........................ 514/27 |
| 6,150,405 | A | * | 11/2000 | Proctor ........................ 514/474 |
| 7,452,527 | B2 | * | 11/2008 | Murad ........................ 424/70.1 |
| 2003/0144346 | A1 | * | 7/2003 | Liao et al. ..................... 514/456 |
| 2003/0224071 | A1 | * | 12/2003 | Murad ........................... 424/728 |

FOREIGN PATENT DOCUMENTS

| | | |
|---|---|---|
| EP | 1 563 827 A | 8/2005 |
| FR | 2 829 692 A | 3/2003 |
| WO | WO96/10387 A | 4/1996 |
| WO | WO 9610387 A2 * | 4/1996 |
| WO | WO 9717953 A1 * | 5/1997 |
| WO | WO2004/078189 A | 9/2004 |
| WO | WO2004/084849 A | 10/2004 |
| WO | WO2005/112960 A | 12/2005 |

OTHER PUBLICATIONS

PCT Search Report dated Oct. 16, 2008.

* cited by examiner

*Primary Examiner* — Chris R Tate
*Assistant Examiner* — Deborah Davis
(74) *Attorney, Agent, or Firm* — Hedman & Costigan, P.C.; James V. Costigan; Kathleen A. Costigan

(57) ABSTRACT

The present invention relates to the use of selected active principles of a natural origin in substitution of extract from Boehmeria Nipononivea for regulating the trophism of hair follicles and the production of sebum on the skin and its use in alopecia, with considerable practical advantages and with respect to the safety profile.

The composition of the invention is based on an association of omega 6 polyunsaturated acids and rutin in a pharmaceutically acceptable carrier.

3 Claims, No Drawings

COMPOSITION COMPRISING RUTIN AND POLYUNSATURATED FATTY ACID HAVING AN INHIBITORY ACTIVITY ON 5 α-REDUCTASE

The present invention relates to a composition having an inhibitory activity on 5 α-reductase.

In particular, the invention relates to a composition suitable for use for sebum-normalization and for the trophism of hair bulbs, for fighting hair thinning and hair loss and in alopecia.

The present invention derives from the field of pharmaceutical, dietetic or cosmetic products suitable for stimulating hair growth and regulating the cutaneous production of sebum.

The present invention derives from the field of preparations suitable for fighting hair loss and stimulating hair growth and re-establishing physiological conditions at the level of the hair bulbs and sebaceous glands.

It is known that androgenetic alopecia is the type of baldness which affects most people suffering from hair loss. This consists of a progressive miniaturization and surfacing of the hair follicles. There is a genetic predisposition towards androgenetic alopecia. What is most probably transmitted are the enzymes interested in the conversion and collection of androgenic hormones, i.e.: the two iso-enzymatic forms of 5-alpha-reductase (type 1 and type 2), P 450 aromatase and the cytosolic receptor of androgens. This enzyme which is mainly expressed at the level of the follicle cells, acts by transforming testosterone, the main male hormone, into its active derivative dihydrotestosterone or DHT, one of the factors responsible for androgenetic alopecia, telogen effluvium and seborrhea.

DHT is harmful for genetically predisposed hair follicles of the scalp. This hormone is implied in the transformation of fleece hair into terminal hair in adolescents and in seborrhea. The 5-alpha-reductase enzyme is abundant in the scalp for favouring the accumulation of DHT.

Furthermore, it is specifically at the level of the follicle structures of the scalp that high quantities of 5-alpha-reductase and consequently high quantities of DHT are produced, which, by interfering with the trophism of follicles causes hair thinning.

Active substances have therefore been studied which, by blocking or reducing the activity of 5-alpha-reductase, cause a decrease in the levels of DHT and consequently a reduction in harmful effects on hair.

It is also known that type 1 of 5-alpha-reductase is mainly localized in the sebaceous glands, in the liver, secondarily in the keratinocytes of the skin and follicle, in the dermal papilla, in the sudoriparous glands. Type 2 of 5-alpha-reductase is localized in the epididymus, seminal vesicles, prostate and genital skin of fetuses, in the epithelial sheath of hair follicles, in fibroblasts of genital skin.

Among the most widely-used substances for fighting hair loss are inhibitors of 5-alpha-reductase, among which finasteride, which has proved to be effective in treating alopecia and the excessive production of sebum.

The use of this molecule, however, is accompanied by side-effects among which reduced libido, impotence, skin rush, reduction in the sperm volume as well as a general counter-indication in the case of pregnancy.

In order to overcome these drawbacks, resort has been made to the use of alternative substances of a natural origin having fewer side-effects.

Studies on a plant originating from Japan, Boehmeria nivea var. nipononivea belonging to the Urticaceae family have demonstrated that the extracts have a significant action for promoting hair growth.

Clinical studies effected by the same Applicant have verified that the aqueous extract from Boehmeria produces extremely significant therapeutic effects. The vegetable extract from Boehmeria has consequently been applied as a regulating agent of hair trophism within formulations for oral or topic use.

Urticaceae are responsible for allergy reactions, also serious, and are consequently counter-indicated particularly in subjects exposed to the risk of atopic asthma. As it is probable that the phytocomplex extracted from the plant in itself contains substances responsible for these allergy reactions, it is therefore also necessary to counter-indicate the use of products containing the extract of Boehmeria in subjects exposed to the risk of allergies, in particular asthmatic subjects.

This represents a serious cause of concern which also discourages all potential users from adopting the product.

The necessity is consequently felt in the current state for availing of preparations of a vegetable origin alternative to Boehmeria nipononivea whose use however minimizes the risks of allergy reactions.

One of the objectives of the present invention therefore consists in providing a composition based on active principles of a natural origin which, although having an activity on the hair bulb and sebum-regulation, minimizes or eliminates the risks of developing the allergic reactions typical of urticaceae.

In view of these objectives, according to a first aspect of the present invention, a composition is provided, which comprises an association of omega 6 polyunsaturated fatty acids and rutin in a pharmaceutically acceptable carrier.

The Applicant proceeded with examining the known constituents of Boehmeria nipononivea and verifying the physiological effects exerted on an experimental scale. From the study, it was found that none of the known constituents alone allows results to be obtained which are comparable to the whole extract. During this research, however, the Applicant arrived at effecting the invention in question which surprisingly allows effects to be obtained which are comparable or higher than those that can be obtained with the whole extract, using a suitable combination of only two of its constituents. These are pure substances of a natural origin and commercially available: rutin and polyunsaturated fatty acids.

Rutin is an active principle belonging to the family of flavonoids, a group of polyfunctional substances having a bioactivity of functional interest in the nutritional and therapeutic field. From a chemical point of view, flavonoids are diphenylpropanoids divided into various groups depending on the oxidation degree of the heterocyclic ring. The nature of the functional groups determines the activity of flavonoids as antioxidants and anti-inflammatory agents.

The Applicant has found that by associating rutin with omega 6 polyunsaturated acids, within a composition, not only is a high activity obtained but the risks of developing allergy reactions associated with the use of extracts from Boehmeria nipononivea are considerably reduced or eliminated.

In addition to an action on 5-alpha-reductase, the polyunsaturated acids used within the scope of the invention exert other important roles of both a structural type, as they are fundamental components of the cellular membranes of all tissues, and also metabolic, as they take part in a series of oxidation and cyclization reactions for the formation of prostaglandins and leucotriens which participate in the regulation of numerous functions of the organism.

According to an embodiment of the invention, the omega-6 polyunsaturated acids (PUFA) which can be used within the scope of the invention are selected from the group comprising:

| Common name | | Chemical name |
|---|---|---|
| Linoleic acid | 18:2 (n-6) | 9,12-octadecadienoic acid |
| Gamma-linolenic acid | 18:3 (n-6) | 6,9,12-octadecatrienoic acid |
| Eicosadienoic acid | 20:2 (n-6) | 11,14-eicosadienoic acid |
| Dihomogammalinolenic acid | 20:3 (n-6) | 8,11,14-eicosatrienoic acid |
| Arachidonic acid | 20:4 (n-6) | 5,8,11,14-eicosatetraenoic acid |
| Docosadienoic acid | 22:2 (n-6) | 13,16-docosadienoic acid |
| Adrenic acid | 22:4 (n-6) | 7,10,13,16-docosatetraenoic acid |
| Docosapentaenoic acid | 22:5 (n-6) | 4,7,10,13,16-docosapentaenoic acid |

Among these omega-6 polyunsaturated acids, gammalinolenic acids, identified with the abbreviation GLA, and linoleic acid have proved to be the most active in regulating the activity of the 5-alpha-reductase enzyme.

A preferred composition of the invention therefore comprises the association of gammalinolenic acid, linoleic acid and rutin in a pharmaceutically or physiologically acceptable carrier.

GLA is an essential fatty acid (EFA) of the omega-6 family. EFAs are essential for health as they are not produced in the body but must be administered with food. EFAs are necessary for normal cerebral functions, growth, development, bone nourishment, regulation of the metabolism and maintenance of the reproductive processes. GLA also exerts an anti-inflammatory action in addition to acting on the growth of keratinocytes, normalizing the lipidic profile.

Linoleic acid is another fatty acid of the omega-6 family which is converted into GLA in the organism.

The Applicant has also found a natural source highly rich in polyunsaturated fatty acids and in particular Linoleic and Linolenic acid in borage oil (Borago offincinalis L.).

In particular, borage oil has the following composition:

| Common name | Isomers | Specifications | Method |
|---|---|---|---|
| Oleic acid | C18:1 | >=150 mg/g | GLC |
| Linoleic acid | C18:2 | >=360 mg/g | GLC |
| Gamma linolenic acid (GLA) | C18:3 | >=225.4 mg/g | GLC |
| Saturated fatty acids | | >=120 mg/g | AOAC |
| Unsaturated fatty acids | | >=220 mg/g | AOAC |
| Polyunsaturated acids | | >=566 mg/g | AOAC |

According to an embodiment of the invention, the Borage oil is applied as an ingredient rich in GLA and linoleic acid, within the composition of the invention.

The composition of the invention is applied in the pharmaceutical or dietetic field in the regulation of the production of sebum on the skin and/or the trophism of hair follicles. In particular, the composition has indications of use in bulbar atrophy, telogen effluvium and androgenetic alopecia.

With respect to the use of the extract of Boehmeria nipononivea, the use of the composition of the invention also provides a series of extremely significant advantages among which:
- the use of active principles of a natural origin which are pure, well-controlled and with a constant quality; the extract on the contrary has the typical variability of products of this type;
- the absence of problems linked to the seasonal supply of plants from which the extract is produced and the consequent periodical lack of availability of the starting material; the extract from Boehmeria is in fact only prepared once a year, when the plant is picked, and must be purchased in huge quantities with consequent problems of storage and preservation;
- low costs of natural active principles;
- no problem of microbiological pollution frequently observed on the Boehmeria extract which, like all extracts of vegetable drugs, is normally characterized by much higher microbial charges than those of pure substances;
- as already mentioned, a considerable reduction in the verification of allergic responses attributed to some of the components present in vegetable extracts from Urticacee (Boehmeria nipononivea).

The use of the composition of the invention also causes a reduction in the secretion of sebum with beneficial effects on acne and seborrhea and a regulation of physiological hair growth, with a favourable effect on androgenetic alopecia, telogen effluvium.

The compositions of the invention for systemic or topic use can be produced in the form of tablets, pills, capsules, solution, suspension, syrup, lotion, foam, cream, and in forms suitable for the controlled release of active principles.

The preparations for the administration of the invention are effected according to common preparation techniques of dietetic and/or pharmaceutical products, adding one or more physiologically acceptable carriers to the synergic active principles.

Physiologically acceptable carriers, mixed with suitable preservers, stabilizers, excipients, carriers and aromatizing agents, are therefore used.

A typical composition for oral use, for example, is in the form of a tablet with a nucleus containing the active principles described above, inside a coating film. The coating typically comprises one or more substances selected from methylhydroxypropyl cellulose, microcrystalline cellulose, stearic acid and suitable dyes such as titanium dioxide, iron oxide and the like.

In the invention composition, the active principles of the invention are typically present in variable quantities, typically ranging from 0.1% by weight to 15% by weight, more preferably from 1 to 10% by weight.

According to another embodiment, a method is provided for regulating the production of sebum on the skin and the trophism of hair follicles comprising the administration or application of a preparation of the type described above to a subject in need of treatment.

According to another aspect of the invention, the use of an omega-6 polyunsaturated fatty acid and rutin is provided for the production of a composition for regulating the activity of 5-alpha-reductase, particularly suitable for regulating the production of sebum on the skin and/or the trophism of hair follicles.

The following examples are provided for purely illustrative purposes of the present invention and should in no way be considered as limiting the protection scope according to the enclosed claims.

EXAMPLE 1

Coated tablet for oral use as food integrator indicated as being useful for the trophism of hair bulbs before and during the menopause.

| | |
|---|---|
| Dibasic Calcium phosphate dihydrate | 186 mg |
| Microcrystalline cellulose | 170 mg |
| Borage oil (omega-6 polyunsat. fat. acid) | 60 mg |

-continued

| | |
|---|---|
| Dry emblic extract | 100 mg |
| Soya isoflavones | 100 mg |
| Hydroxypropylmethylcellulose | 70 mg |
| Zinc amino acid chelate | 37.5 mg |
| Copper amino acid chelate 10% | 12 mg |
| Mono- and di-glycerides of fatty acids | 11 mg |
| Rutin | 10 mg |
| Calcium d-pantothenate | 9.9 mg |
| Silicon dioxide (colloidal silica) | 7.5 mg |
| Spermidine trichlorohydrate | 0.55 mg |
| Folic acid | 0.33 mg |
| Biotin | 0.165 mg |
| Resveratrol | 0.05 mg |
| Sepifilm LP030 | 25 mg |
| Sepifilm TM LP 770 white | 24.575 mg |
| Yellow iron oxide (E 172) | 0.25 mg |
| Red iron oxide (E 172) | 0.175 mg |

EXAMPLE 2

Tablet for oral use.

| | |
|---|---|
| l-Methionine | 300 mg |
| Borage oil (omega-6 polyunsat. fat. acid) | 40-100 mg |
| Rutin | 3-12 mg |
| Ascorbic acid | 90 mg |
| Vitamin E acetate (dl-alpha tocopherol) | 15 mg |
| Vitamin B6 (Pyridoxine) | 2.7 mg |
| Spermidine trichlorohydrate | 0.5 mg |
| Calcium d-pantothenate | 9 mg |
| d-Biotin | 0.15 mg |
| Zinc amino acid chelate | 37.5 mg |
| Copper amino acid chelate | 12.5 mg |
| Folic acid | 0.33 mg |
| Microcrystalline cellulose | 50-150 mg |
| Hydroxypropylmethylcellulose | 40-60 mg |
| Dextrin | 5-15 mg |
| Silicon dioxide | 5-7 mg |
| Dibasic di-Calcium phosphate dihydrate | 50-120 mg |
| Magnesium stearate | 5-8 mg |

EXAMPLE 3

Tablet for oral use with a sebum-regulating activity for the control of dandruff.

| | |
|---|---|
| *Lactobacillus rhamnosus* | 1 × 10^9 ufc/cpr |
| Borage oil (omega-6 polyunsat. fat. acid) | 40-100 mg |
| Rutin | 3-12 mg |
| Methionine | 200 mg |
| Vit B5 (Calcium pantothenate) | 9 mg |
| Vit B6 (Pyridoxine) | 2 mg |
| Biotin | 0.23 mg |
| Beta-carotene | 7.2 mg |
| Vit B2 (Riboflavin) | 1.6 mg |
| Dry *Ajuga* extract | 2.5 mg |
| Zinc amino acid chelate | 37.5 mg |
| Vitamin C | 60 mg |
| Vitamin E (dl-alpha-tocopheryl acetate) | 15 mg |
| Selenium yeast | 0.2 mg |
| Copper amino acid chelate | 12.5 mg |
| Microcrystalline cellulose | 50-150 mg |
| Hydroxypropylmethylcellulose | 40-60 mg |
| Dibasic di-Calcium phosphate dihydrate | 50-120 mg |
| Magnesium stearate | 5-10 mg |
| Silicon dioxide | 5-10 mg |

EXAMPLE 4

Tablet for oral use for the prevention of androgenetic alopecia in young adults.

| | |
|---|---|
| Spermidine trichlorohydrate | 0.5 mg |
| Calcium d-pantothenate | 9 mg |
| d-Biotin | 0.15 mg |
| Quercitin | 0.9 mg |
| Borage oil (omega-6 polyunsat. fat. acid) | 40-100 mg |
| Rutin | 3-12 mg |
| L-Arginine chlorohydrate | 242 mg |
| Dry *Ajuga reptans* extract | 5 mg |
| Zinc (as amino acid chelate) | 7.5 mg |
| Copper (as amino acid chelate) | 1.2 mg |
| Tapioca dextrin | 40-100 mg |
| Microcrystalline cellulose | 130-200 mg |

EXAMPLE 5

Capsules for oral use with a stimulating action on hair bulbs and sebum-normalizing.

| | |
|---|---|
| Gamma-linolenic and linoleic acids | 20-50 mg |
| Tapioca dextrin | 40-100 mg |
| Rutin | 3-12 mg |
| Microcrystalline cellulose | 50-150 mg |
| Dibasic di-Calcium phosphate dihydrate | 50-150 mg |
| Magnesium stearate | 3-8 mg |
| Silicon dioxide | 3-6 mg |
| Natural gelatin (outer coating) | as sufficient |

EXAMPLE 6

Lotion for topic use with a trophic action on hair bulbs and sebum-normalizing.

| | |
|---|---|
| Citric acid | 0.04-0.052 mg |
| Disodium EDTA | 0.03-0.06 mg |
| Alcohol | 15-20 mg |
| PEG-40 Hydrogenated castor oil | 0.5-3 mg |
| Tween 20 | 0.5-1.0 mg |
| Perfume | 0.10 mg |
| Omega-6 polyunsaturated fatty acids | 0.5-1.8 mg |
| Rutin | 0.2-0.5 mg |
| Water | complement to 100 ml |

EXAMPLE 7

Antidandruff shampoo

| | |
|---|---|
| Disodium EDTA | 0.1-0.3 mg |
| Polyquaternium-10 | 0.1-0.3 mg |
| Polyquaternium-55 | 0.1-0.5 mg |
| Citric acid | 0.6-0.8 mg |
| Arginine | 0.05-0.1 mg |
| Potassium undecylenoyl hydrolyzed wheat protein | 3.6 mg |
| Sodium lauroyl sarcosinate | 1.5 mg |
| Cocamide mipa | 1-3 mg |
| Piroctone olamine | 0.1-0.5 mg |
| Disodium laureth sulfosuccinate | 1-5 mg |
| Disodium capryloyl glutamate | 0.4-1 mg |
| Zinc coceth sulfate | 1-8 mg |
| Peg-200 hydrogenated glyceryl palmate | 0.5-3 mg |
| Pet-7 glyceryl cocoate | 0.5-2 mg |
| Laureth-2 | 0.05-2 mg |

| -continued | |
|---|---|
| Peg-40 hydrogenated castor oil | 0.2-1 mg |
| Phenyl trimethicone | 0.05-3 mg |
| Silicone quaternium-15 | 0.005-1 mg |
| Laureth-4 | 0.01-0.5 mg |
| Borage oil (omega-6 polyunsat. fat. acid) | 0.5-1.8 mg |
| Rutin | 0.2-0.5 mg |
| Perfume | as sufficient |
| Water | complement to 100 ml |

A study was effected on the composition of example 1 to evaluate the capacity of the active principles contained therein of modulating the activity of the 5-alpha-reductase enzyme in vitro, after treatment for up to 72 hours with the material tested on a cellular line of murine fibroblasts. This enzyme is present in the skin, in melanocytes, fibroblasts, keratinocytes, it converts testosterone into dihydrotestosterone (DHT) and exerts a key role in many skin disorders such as acne vulgaris, hirsutism, seborrhea and alopecia.

In the test in question, the fibroblasts were treated with testosterone in order to increase the basal production of 5-alpha-reductase, and then with the material under study at different concentrations for a period of up to 48 hours.

The content of DHT produced by the cells treated was measured at different endpoints (in the specific case at 24 and 48 h) with an ELISA method and, by comparison with the non-treated cells, the inhibition percentage of the specific enzymatic activity can be estimated.

A titrated extract of Serenoa Repens (Saw palm), a well-known plant in pharmacopoeia for its capacity of inhibiting 5-alpha-reductase and used for this purpose in the treatment of prostatic hyperplasia in men, was used as positive control.

The following products were used as comparative material:
Dry Boehmeria nipononivea extract
Borage oil powder (omega-6)
Rutin
Experimental Procedure
Test Method:
Experimental Model The cellular model used for the test in vitro is represented by:
murine fibroblasts (3T3 cells). The cell line derives from fibroblasts of albino mice Swiss strain stabilized by embryos.

Preparation of the Test Sample

The samples were dissolved in a solution of absolute ethanol and water (1:1) and then diluted in the medium at the following concentrations:
  Dry Boehmeria nipononivea extract 10 µg/ml
  Borage oil powder (omega-6) 6 µg/ml
  Rutin 0.5 µg/ml
  Mixture of Borage oil powder (omega-6) and Rutin of the invention: 6.5 µg/ml Positive Control Serenoa repens at a final concentration of 10 mcg/ml was used as positive control, in the presence of testosterone 1 mcg/L.

Test Procedure
Pre-Incubation Phase

The cells are planted in 25 $cm^2$ flasks (T25) in a DMEM culture medium (Dulbecco's Minimum Essential Medium) with the addition of 10% of FBS (fetal bovine serum). Once the confluence has been reached, the cultures are treated for 24 hours with 10 ng/ml of testosterone.

Treatment Phase

After the pre-incubation phase, the cell cultures are treated with the starting materials indicated at the final concentration envisaged. The extract of Serenoa repens at 0.1 mg/ml is used as positive control, whereas the negative control consists of plates treated with the solvent. The exposure is prolonged for 24-48 hours in an incubator at 37° C., 5% of $CO_2$, renewing the medium every 24 hours. Each sample is tested in duplicate. At the end of the experiment, a cell count is effected to evaluate possible cytotoxic effects. The determination of the quantity of DHT and testosterone present is effected by immunodiagnostic tests (ELISA) in the extracellular (conditioned culture mediums) and intracellular (cell extracts) compartments.

Preparation of the Cell Extracts

At the end of the experiment, the culture medium is collected from each flask and a cell extract is prepared. This is prepared in four phases:
  tripsinization of the cell layer in situ in the flask
  centrifugation and collection of the cells in pellets
  extraction with Triton X-100 (1% in basal medium)
  ultrasonication for 30 minutes DHT Determination 50 mcL of culture medium were taken from each cavity, to be used for determining the DHT by means of the ELISA test, carried out at room temperature at each end-point (24-48 hours). The method comprises the processing of a standard curve, calculated within a range of appropriate concentrations. The ELISA test uses a specific antibody directed against human DHT immobilized on a solid substrate and a reagent (DHT conjugated with Horse-Radish-Peroxidase) which competes for binding with the antibody. The reaction is revealed by means of a substrate solution and develops a coloured compound, inversely proportional to the concentration of DHT. The absorbance at 450 nm is read for each sample.

The samples are read at a wave-length of 450 nm.

Calculation of the Results
Determination of the Final Dihydrotestosterone (DHT)

As specified above, the real concentration of DHT is calculated according to the formula:

$$[DHT\ measured]-[DHT\ bovine\ serum]-[testosterone\ crosslinking]$$

wherein the quantity of DHT present in the medium (coming from bovine serum) is equal to 0.1 ng/ml.

The crosslinking of the testosterone is calculated according to the formula:

$$[concentration\ testosterone] \times 8.7/100.$$

At this point, it is possible to calculate the inhibition percentage of 5-alpha-reductase. The result is expressed as the experimental average measured. The overall experimental error is estimated at as being not higher than 10%.

The % of activity of 5-alpha-reductase is calculated with respect to the control non-treated with the substance being examined:

$$reduction\ \%=[average\ absorbance\ ctrl-average\ absorbance\ treated\ product]/average\ absorbance\ ctrl*100$$

Results

|  | 24 hours | | 48 hours | |
| --- | --- | --- | --- | --- |
|  | DHT pg/ml | Inhibition % | DHT pg/ml | Inhibition % |
| Negative control | 99.0 |  | 35.1 |  |
| Positive control: *Serenoa repens* 10 mcg/ml | 98.2 | 0.8% | 27.8 | 20.8% |
| Dry *Boehmeria* extract 10 mcg/ml | 95.0 | 4.0% | 26.6 | 24.2% |
| Mixture omega-6 and Rutin 6.5 mcg/ml | 95.2 | 3.8% | 23.6 | 32.8% |

The results show that among the substances tested, the mixture of omega-6 polyunsaturated fatty acids with rutin proves to be more effective than the Boehmeria extract in inhibiting the activity of 5-alpha-reductase enzyme with a maximum activity at 48 hours (−32.8%).

The effect of Boehmeria and of the mixture of omega-6 polyunsaturated fatty acids with rutin is established more rapidly with respect to the positive control, consisting of Serenoa repens.

The invention claimed is:

1. A method for regulating the trophism of hair follicles in a subject in need thereof comprising administering to said subject an effective amount of a composition consisting essentially of:
   a mixture of gamma-linolenic acid and linoleic acid, wherein the mixture is present in an amount of from 0.01 to 10%, by weight;
   rutin, wherein the rutin is present in an amount of from 0.001 to 10%, by weight; and
   one or more physiologically acceptable carriers.

2. The method according to claim 1, wherein said composition is a food integrator or a dietetic product for oral, use.

3. The method according to claim 1, wherein said composition is a pharmaceutical or cosmetic product for topical application.

* * * * *